United States Patent [19]

Bandurco et al.

[11] Patent Number: 4,617,392

[45] Date of Patent: Oct. 14, 1986

[54] 4-ALKYL-5,6-METHYLENEDIOXY-2-1[H]-QUINAZOLINONES USEFUL AS CARDIOTONIC AGENTS

[75] Inventors: Victor T. Bandurco, Bridgewater, N.J.; Stanley C. Bell, Narberth, Pa.; Donald W. Combs, Piscataway; Robert Falotico, Belle Mead, both of N.J.

[73] Assignee: Ortho Pharmaceutical Corporation, Raritan, N.J.

[21] Appl. No.: 537,228

[22] Filed: Sep. 29, 1983

[51] Int. Cl.$^4$ .................. C07D 487/00; A61K 31/505
[52] U.S. Cl. .................................... 544/250; 544/95; 544/286; 514/274; 549/435; 549/439; 549/446
[58] Field of Search ................. 544/250, 286; 514/274

[56] References Cited

U.S. PATENT DOCUMENTS

| | | | |
|---|---|---|---|
| 3,838,126 | 9/1974 | Wagner | 544/251 |
| 4,096,144 | 6/1978 | Yamamoto et al. | 544/286 |
| 4,164,578 | 8/1979 | Vogt | 544/250 |
| 4,236,006 | 11/1980 | Gamboni et al. | 544/286 |
| 4,387,223 | 6/1983 | Yamamoto et al. | 544/286 |
| 4,490,374 | 12/1984 | Bandurco et al. | 424/251 |

FOREIGN PATENT DOCUMENTS

| | | |
|---|---|---|
| 2017482 | 2/1977 | Japan . |
| 7200367 | 12/1982 | Japan . |
| 197269 | 12/1982 | Japan . |

OTHER PUBLICATIONS

Bandurco et al, Chem. Abst. 95:203866w.
Wagner, Chem. Abst. 82:4298u (1975).
Schlecker et al., Chem. Abst. 99:175790d.

*Primary Examiner*—Donald G. Daus
*Assistant Examiner*—Cecilia Shen
*Attorney, Agent, or Firm*—Benjamin F. Lambert

[57] ABSTRACT

4-Alkyl-5,6-, 6,7-methylenedioxy-2-1[H]-quinazolinones are prepared from 2,3-methylenedioxyacetophenones. The 4-alkyl-5,6-, 6,7-methylenedioxy-2-1[H]-quinazolinones are active as cardiotonic agents.

4 Claims, No Drawings

4-ALKYL-5,6-METHYLENEDIOXY-2-1[H]-QUINAZOLINONES USEFUL AS CARDIOTONIC AGENTS

The present invention relates to 4-alkyl substituted methylenedioxy quinazoinones having the following structural formula:

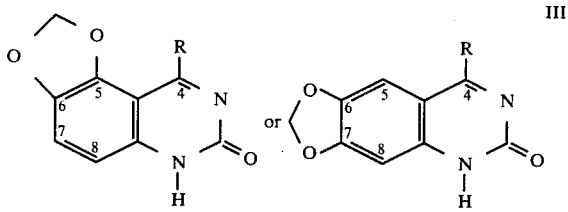

wherein R is hydrogen or lower alkyl having 1-5 carbon atoms. As can be seen from the above structures, the methylenedioxy moiety may be attached to the benzene ring at either the 5,6- or 6,7-positions.

The 4-alkyl methylenedioxy quinazolinones (III) of the present invention can be prepared according to the following reaction scheme which, for the sake of simplicity will be illustrated for the preparation of the 5,6-isomer. However, the 6,7-isomer can be prepared in the same manner.

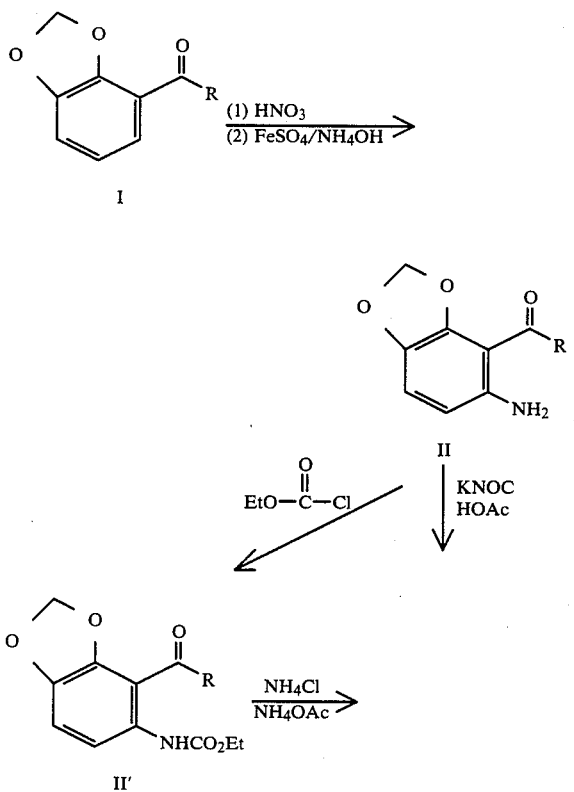

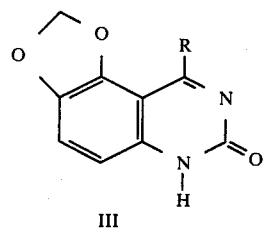

wherein R is hydrogen or lower alkyl.

As can be seen from the reaction scheme, the 4-alkyl substituted 5,6- and 6,7-methylenedioxy quinazolinones (III) can be prepared by first reacting a 2,3-methylene dioxyacylbenzene (I) such as 2,3-methylenedioxyacetophenone or 2,3-methylenedioxybutyrophenone with a nitrating agent such as nitric acid. The nitration step is preferably carried out at a temperature between $-5°$ C. and room temperature. The nitration step yields a mixture of 5- and 6-nitromethylenedioxyacylbenzene compounds. The mixture of nitro compounds is then reacted with a reducing agent to form the corresponding amine (II). Suitable reducing agents which can be employed include ferrous sulfate, zinc chloride/HCl, palladium on charcoal and platinum dioxide. The amino compound is then converted to the quinazolinone by first reacting it with an alkali metal cyanate such as, for example, potassium cyanate, in a suitable solvent such as acetic acid or propionic acid or a mixture of an organic solvent and a mineral or organic acid. The reaction mixture is then neutralized with a mild base such as, for example, ammonium hydroxide, 5% sodium bicarbonate or 1N sodium hydroxide to yeild the 4-alkyl-5,6- or 6,7-methylenedioxy quinazolinone compound.

Alternatively the quinazolinone (III) can be prepared by first reacting the amine (II), where R is lower alkyl, with ethylchloroformate to form the corresponding 2-carboethoxyamino-5,6-methylenedioxybenzaldehyde (II'). The quinazolinone (III) is then obtained by reacting the 5,6-methylenedioxybenzaldehyde compound (II') with an ammonium salt such as ammonium acetate or ammonium chloride in a suitable solvent such as acetic acid.

In those cases where R is hydrogen, the starting material in the preparation of the 6,7-isomer is 6-aminopiperonal. In the case of the 5,6-isomer, the quinazolinone wherein R is hydrogen is prepared by first reacting 5,6-methylenedioxy-2-nitrobenzaldehyde with ethylene glycol to form the corresponding 2-nitro ethylene glycol acetal. The nitro compound is then reduced to the corresponding amino compound by reaction with a reducing agent such as platinum dioxide or palladium on charcoal. The 2-amino-5,6-methylenedioxy benzaldehyde ethylene glycol acetal is then converted to the 2-carbethoxyamino-5,6-methylenedioxybenzaldehyde by reaction with an alkylhaloformate such as ethylchloroformate. The 5,6-methylenedioxy-2(1H)-quinazolinone is then obtained by reacting the 2-carbethoxyamino-5,6-methylenedioxybenzaldehyde with an ammonium salt such as ammonium acetate or ammonium chloride in a suitable organic acid such as acetic acid or propionic acid.

Also included in the invention are the pharmaceutically acceptable acid addition salts of the quinazolinones. The 4-alkyl-5,6- and 6,7-methylenedioxy quinazolinones increase myocardial contractility and as such are active as cardiotonic agents.

Pharmaceutical compositions containing a compound of the present invention as the active ingredient in intimate admixture with a pharmaceutical carrier can be prepared according to conventional pharmaceutical compounding techniques. The carrier may take a wide variety of forms depending on the form of preparation desired for administration, e.g., intravenous, oral or parenteral. In preparing the compositions in oral dosage form, any of the usual pharmaceutical media may be employed, such as, for example, water, glycols, oils, alcohols, flavoring agents, preservatives, coloring agents and the like in the case of oral liquid preparations such as, for example, elixirs and solutions; or carriers such as starches, sugars, diluents, granulating agents, lubricants, binders, disintegrating agents and the like in the case of oral solid preparations such as, for example, suspensions, powder, capsules and tablets. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, though other ingredients, for example, to aid solubility or for preservative purposes, may be included. Injectable suspensions may also be prepared, in which case appropriate liquid carriers, suspending agents and the like may be employed. The pharmaceutical compositions will generally contain, dosage unit, e.g., tablet, capsule, powder, injection, teaspoonful and the like, from about 15 to about 300 mg/kg and preferably from about 30 to about 200 mg/kg of the active ingredient.

The following examples describe the invention in greater particularity and are intended to be a way of illustrating but not limiting the invention.

EXAMPLE 1

5- and 6-Nitro-2,3-methylenedioxyacetophenone 2,3-Methylenedioxyacetophenone (2.49 g, 15.2 mmoles) was added in small portions to 40 ml of nitric acid (70%) at −5° C. After 1 hour at −5° C. the solution was poured into ice water (150 ml) and the resultant precipitate collected by filtration, washed with water and recrystallized from methanol to give a mixture of 5- and 6-nitro-2,3-methylenedioxyacetophenone in 77% yield.

EXAMPLE 2

6-Amino-2,3-methylenedioxyacetophenone

The mixture of nitro compounds (2.47 g) was dissolved in boiling ethanol and water (65 ml, 60:40) and added to a boiling solution of $FeSO_4.7H_2O$ (23 g) in water (65 ml). After 10 minutes, concentrated ammonium hydroxide (35 ml) was added in 5 ml portions over 30 minutes. After 10 additional minutes the hot mixture was filtered through celite and the filtrate concentrated in vacuo to approximately 70 ml. The product 6-amino-2,3-methylene dioxyacetophenone (0.866 g, 41%) was collected by filtration, mp 94°–99° C.

EXAMPLE 3

5,6-Methylenedioxy-4-methyl-2-1[H]-quinazolinone

The aminoketone (1.34 g, 7.51 mmoles) prepared in Example 2 was dissolved in acetic acid (15 ml, 50%). Potassium cyanate (0.669 g, 8.26 mmoles) was added with stirring and the mixture heated at 50° C. for 1.5 hours. The reaction was cooled in ice, neutralized with 2N ammonium hydroxide solution and the resultant precipitate collected by filtration and washed with acetone. The residue was recrystallized once from hot dilute ammonia and once from methanol to give the product at a chartreuse powder (0.461 g, 30%), mp 267°–270° C.

When in the above procedure 6-amino-2,3-methylenedioxy propiophenone and 6-amino-2,3-methylenedioxybutyrophenone are employed in place of 6-amino-2,3-methylenedioxy acetophenone the corresponding 5,6-methylenedioxy-4-propyl-2-1[H]-quinazolinone and 5,6-methylenedioxy-4-n-butyl-2-1-[H]-quinazolinone are obtained.

EXAMPLE 4

6,7-Methylenedioxy-2(1H)-quinazolinone

6-Aminopiperonal (4.0 g, 0.024 moles) was suspended in 20 ml of acetic aicd (50%). Potassium cyanate (2 g, 0.024 moles) was added in small portions at room temperature and the mixture was stirred at 50° C. for 2 hours. The mixture was cooled and neutralized with concentrated $NH_4OH$. The filter cake was washed with cold water and cold methanol and the solid was suspended in ethyl acetate (2 liters), boiled on a steam bath and then filtered. The insoluble portion was dissolved in a minimum of ammonium hydroxide solution and the solution was boiled to drive off excess ammonia to afford 6,7-methylenedioxy-2(1H)-quinazolinone, mp >300 (yield 2.08 g, 45%), M+190.

EXAMPLE 5

4-Methyl-6,7-methylenedioxy-2(1H)-quinazolinone

A stream of dry ammonia gas was passed for 3 hours through a solution of 2-[N-carbethoxyamino]-4,5-methylenedioxyacetophenone (12.6 g, 0.050 m) in dimethylformamide (25 ml) and ammonium acetate (108 g) maintained at 155°–160° C. The reaction mixture was cooled and poured into ice-$H_2O$ (500 ml). The crude product was collected by filtration and crystallized from chloroform to give the quinazolinone as a yellow solid; yield 5.4 g (52.9%) mp 310°–312° C.

When in the above procedure 2-[N-carbethoxyamino]-4,5-methylenedioxypropiophenone and 2-[N-carbethoxyamino]-4,5-methylenedioxy-butyrophenone are employed in place of 2-[N-carbethoxyamino]-4,5-methylenedioxyacetophenone the corresponding 6,7-methylenedioxy-4-propyl-2-1[H]-quinazolinone and 6,7-methylenedioxy-4-n-butyl-2-1[H]-quinazolinone are obtained.

EXAMPLE 6

5,6-Methylenedioxy-2(1H)-quinazolinone

A. 5,6-Methylenedioxy-2-nitrobenzaldehyde (5 g, 31 mmoles) was dissolved in 300 ml of benzene containing 2.67 g of ethylene glycol and 80 mg p-toluenesulfonic acid. The solution was refluxed in a Dean-stark trap for 18 hours, cooled to room temperature and washed with 2×100 ml of saturated $NaHCO_3$ solution. The organic layer was dried over $MgSO_4$, filtered and evaporated. The crude product was recrystallized from hexane to give 5,6-methylenedioxy-2-nitrobenzaldehyde ethylene glycol acetal; mp 82°–84° C.

B. 5,6-Methylenedioxy-2-nitrobenzaldehyde ethylene glycol acetal (5.0 g, 21 mmoles) was dissolved in ethyl acetate and shaken with 300 mg of platinum dioxide and 80 mg of sodium acetate under an atmosphere of hydrogen (50 psi) for 5 hours. The mixture was filtered through Celite and dried over MgSO$_4$. The filtrate was then evaporated to given an oil which was recrystallized from hexane to give 2-amino-5,6-methylenedioxybenzaldehyde ethylene glycol acetal (3.2 g, 73%) mp 75°–77° C.

C. 2-Amino-5,6-methylenedioxybenzaldehyde ethylene glycol acetal (2.95 g, 14.1 mmoles) was dissolved in 50 ml of tetrahydrofuran and 2.7 ml (28.2 mmoles) of ethylchloroformate and 2.28 ml of 9.25M sodium hydroxide were added. After heating at reflux for 2 hours the solvent was removed in vacuo. The residue was dissolved in acetone and 1N hydrochloric acid (3 ml) was added. After stirring at room temperature for 3 hours the solvent was removed in vacuo, the residue was suspended in water and the insolubles were collected by filtration to give a 94% yield of 2-carboethoxyamino-5,6-methylenedioxybenzaldehyde, mp 123°–127;20 C.

D. 2-Carboethoxyamino-5,6-methylenedioxybenzaldehyde (5.0 g, 21.1 mmoles) was added to a suspension of ammonium acetate (1.63 g, 21.1 mmoles) and ammonium chloride (1.13 g, 21.1 mmoles) in 50 ml of acetic acid. The temperature was slowly raised to 90° C. and held there for 15 hours. The mixture was diluted with one volume of water and then extracted with ethyl acetate, after adjusting the pH to 9 with concentrated ammonium hydroxide. The ethyl acetate layers were evaporated to dryness and the residue was recrystallized first from 10% NH$_4$OH then from methanol to give 250 mg of 5,6-methylenedioxy-2(1H)-quinazolinone (6%), mp >300° C., M+190.

We claim:

1. A compound of the formula:

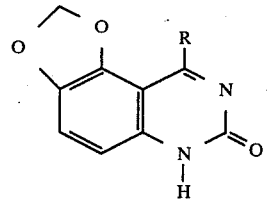

wherein R is hydrogen or lower alkyl.

2. The compound of claim 1 which is 5,6-methylenedioxy-4-methyl-2-1[H]-quinazolinone.

3. The compound of claim 1 which is 5,6-methylenedioxy-4-ethyl-2-1[H]-quinazolinone.

4. The compound of claim 1 which is 5,6-methylenedioxy-2-1[H]-quinazolinone.

* * * * *